United States Patent
Carlucci

(10) Patent No.: US 7,202,424 B2
(45) Date of Patent: Apr. 10, 2007

(54) BALANCE CONTROL SYSTEM FOR WEIGHT SCALES

(75) Inventor: Vito James Carlucci, Stratford, CT (US)

(73) Assignee: Conair Corporation, Stamford, CT (US)

( * ) Notice: Subject to any disclaimer, the term of this patent is extended or adjusted under 35 U.S.C. 154(b) by 11 days.

(21) Appl. No.: 10/726,266

(22) Filed: Dec. 2, 2003

(65) Prior Publication Data

US 2004/0163855 A1 Aug. 26, 2004

Related U.S. Application Data

(63) Continuation-in-part of application No. 10/308,993, filed on Dec. 2, 2002.

(51) Int. Cl.
*G01G 19/00* (2006.01)
(52) U.S. Cl. .................................. 177/199; 177/238
(58) Field of Classification Search .............. 73/172; 177/199, 200, 177, 238; 178/18.05
See application file for complete search history.

(56) References Cited

U.S. PATENT DOCUMENTS

| | | | | |
|---|---|---|---|---|
| 2,653,475 | A | | 9/1953 | Kraus ........................... 73/172 |
| 3,655,003 | A | * | 4/1972 | Yamajima .................... 177/173 |
| 3,657,475 | A | | 4/1972 | Peronneau et al. ........... 178/18 |
| 4,082,153 | A | * | 4/1978 | Provi ........................... 177/177 |
| 4,558,757 | A | | 12/1985 | Mori et al. .................... 178/18 |
| 4,576,244 | A | * | 3/1986 | Zeigner et al. .............. 177/245 |
| 4,650,014 | A | * | 3/1987 | Oldendorf et al. ........... 177/177 |
| 4,763,739 | A | * | 8/1988 | Kasinoff .................. 177/210 R |
| 4,848,477 | A | * | 7/1989 | Oldendorf et al. ........ 177/25.14 |
| 4,909,338 | A | * | 3/1990 | Vitunic et al. ................. 177/50 |
| 5,276,432 | A | | 1/1994 | Travis ........................... 340/573 |
| 5,643,417 | A | * | 7/1997 | Hanaya ....................... 162/300 |
| 5,750,937 | A | | 5/1998 | Johnson et al. ........... 177/25.11 |
| 6,407,351 | B1 | * | 6/2002 | Meyer et al. ................ 177/238 |
| 6,605,784 | B2 | * | 8/2003 | Eigenmann et al. ...... 177/25.13 |

OTHER PUBLICATIONS

PCT International Search Report dated Jul. 20, 2004 from corresponding International Application No. PCT/US03/38210.

* cited by examiner

*Primary Examiner*—Randy W. Gibson
(74) *Attorney, Agent, or Firm*—Lawrence Cruz; Steven A. Garner

(57) ABSTRACT

The present invention is directed to a weight scale having a balance control system that detects unequal load distribution to the scale's load sensors and produces an output signal that enables the user to re-distribute weight until a predetermined level of balance is achieved. Various load sensors are positioned in an array in the scale and are in communication with a controller that receives signals from the sensors indicative of relative load applied to each sensor. The controller generates a signal that is displayed or emitted to the user indicative of the position of the user's center of gravity relative to the sensors.

2 Claims, 2 Drawing Sheets

BALANCE CONTROL SYSTEM FOR WEIGHT SCALES

This application is a continuation-in-part of Ser. No. 10/308.993 filed Dec. 2, 2002.

BACKGROUND OF THE INVENTION

1. Field of the Invention

The present invention relates to weight scales. More particularly, the present invention relates to a weight position sensor system. The weight position sensor system has a balance control system that detects load distribution on the scale and provides an output signal to a user to indicate whether or not the user should re-position or shift weight in order to more equally distribute load and, thus, optimize scale accuracy.

2. Description of Related Art

Various known weight scales generally provide an upper platform for the user to stand on, having load detection cells positioned beneath the scales. The load from the weight of the user is transmitted from the platform to the load detection cells, which are mounted to a base. The load on the cells is measured by the cells and communicated to a controller, which causes an output display of the user's weight. The load detection cells are usually positioned in an evenly spaced array in an effort to position them where the load of the user is likely to be evenly distributed. This requires anticipation of precisely where the user is likely to stand on the scale and of how the user will distribute his or her weight in terms of distribution between front and back of the foot as well as right-vs.-left foot. The resultant scale reading is sometimes inaccurate because each user may stand on the scale in a different position and with different weight distribution, and each user has different size feet.

BRIEF SUMMARY OF THE INVENTION

It is an object of the present invention to provide a weight position sensor system.

It is another object of the present invention to provide a weight position sensor system that has a balance control system that detects load distribution on the scale.

It is still another object of the present invention to provide a weight position sensor system that has an output signal to a user to indicate whether or not the user should re-position or shift weight in order to more equally distribute load.

It is a further object of the present invention to provide a weight position sensor system that has optimum scale accuracy.

These and other object and advantages of the present invention are achieved by a weight scale having a weight position sensor system. The weight position sensor system has a balance control system that detects unequal load distribution to the scale's load cells and produces an output signal that enables the user to re-distribute weight until a predetermined level of balance is achieved.

DETAILED DESCRIPTION OF THE INVENTION

Figure 1:
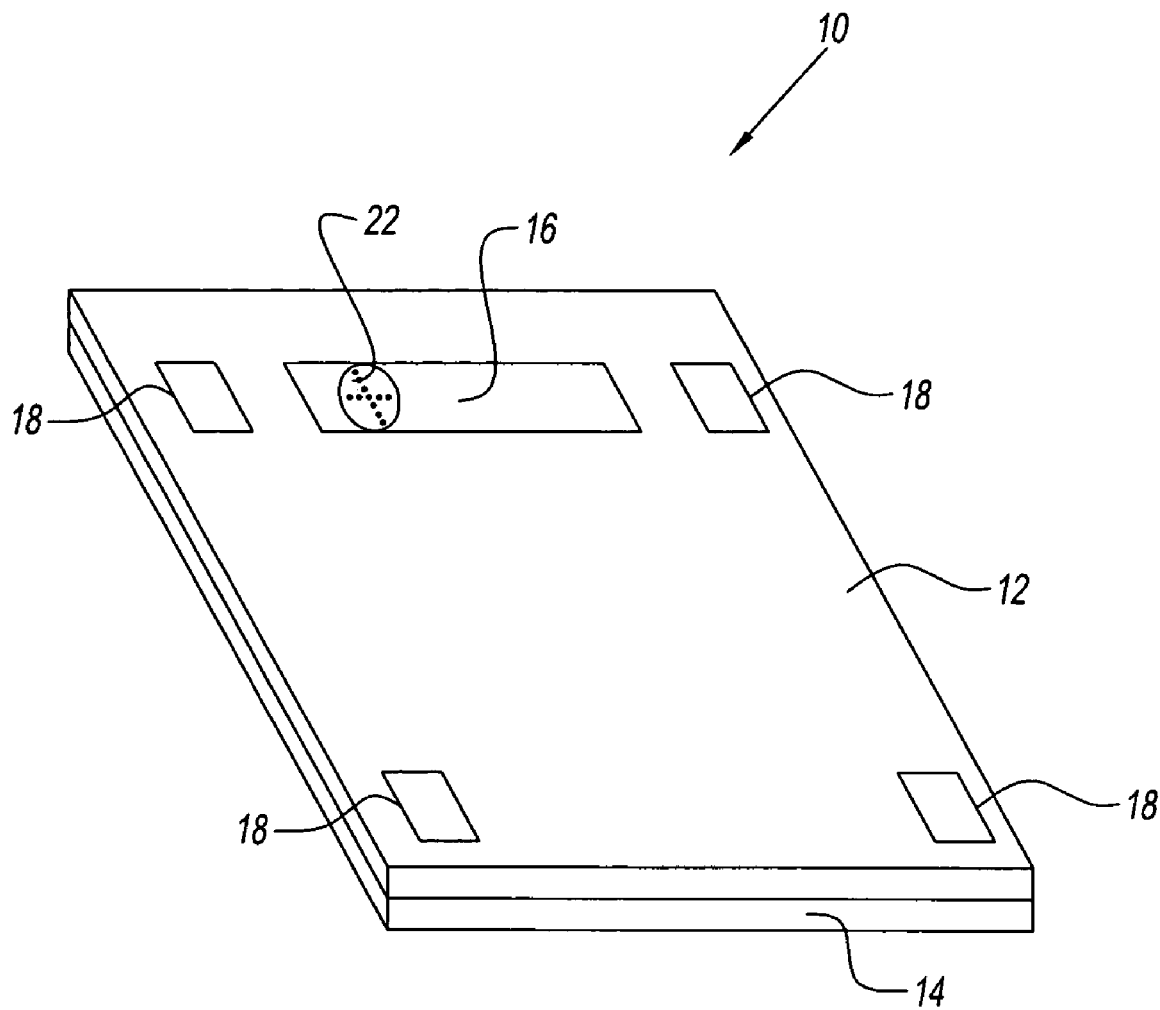
FIG. 1 is a schematic, perspective view of a weight scale according to the present invention.

Referring to FIG. 1, there is provided a weight scale generally represented by reference numeral 10. Weight scale 10 includes an upper platform or weight supporting surface 12, a base 14 adapted to receive the platform, a display screen 16 preferably visible through the platform, and a plurality of load detection cells or sensors 18 (shown in phantom) positioned between the platform and the base. The cells 18 are mounted between the platform 12 and the base 14 in such a way that the load of the user's weight on the platform will be transmitted directly to the cells, as is generally known in the art.

The cells 18 may be of the type generally known in the art, which generally include a deflectable member (not shown) through which electric current is passed. When the deflectable member flexes under load applied to the platform 12, it resistance properties are altered, and the change is monitored by measuring current flow. This is translated into a weight reading displayed to the user on the display screen 16. Each load cell 18 is preferably a strain gauge. Such strain gauges are known in the art. In the preferred embodiment, there are four load cells that are applied one to each corner of the upper platform 12 thereby forming a generally rectangular pattern.

The upper platform or surface 12 is made of any material that permits any weight thereon to be directly transmitted to the cells 18. The upper platform 12 can be made of plastic, metal, glass or other suitable material that can hold the weight of the user without breaking. Preferably, the upper surface 12 is made of plastic.

The base 14 is made of any material. Preferably, the base 14 is made of a material that protects the cells 18 from moisture or other undesired environmental effects that could adversely affect the performance of the cells. Accordingly, the cells 18 are preferably made of ceramic or plastic.

The scale 10 has a plurality of feet (not shown). Preferably, each foot is positioned in a corner of the scale 10. Each load cell 18 is located directly above a different foot. Each foot is movable relative to the upper platform 12.

Figure 2:
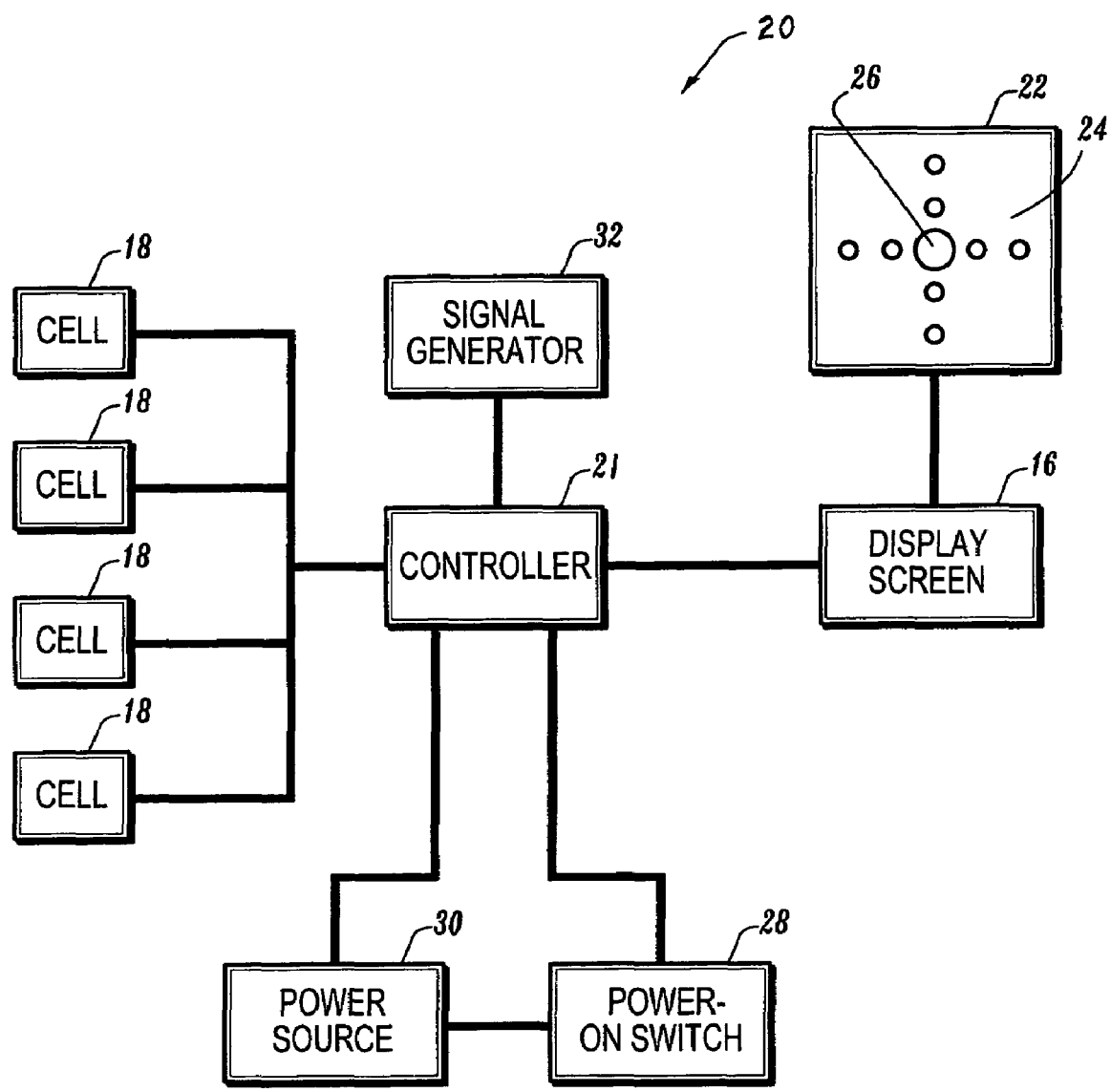
FIG. 2 is a schematic diagram of a balance control system for weight scales according to the present invention.

FIG. 2 shows a schematic diagram of a balance control system 20 for the weight scale 10 according to a preferred embodiment of the present invention. The balance control system 20 shows four load detections cells 18. A computer controller 21 of the type generally known, communicates with the cells 18 to process load signals from each cell, compare the signals from each cell, and provide an output signal that results from the comparison of each load signal, to the display screen 16 that indicates to the user whether or not the user's weight is evenly distributed.

In the preferred embodiment shown in FIG. 1, the load detection cells 18 are arranged in a uniform or evenly spaced, square configuration about the platform 12 such that if a user stands so that his/her center of gravity is in the center of the platform, and thus the center of the load detection cells, the load caused by the user's weight will be equally distributed and supported by each of the four load detection cells 18 so that the scale 10 will have equal load or weight distribution. It is understood that any number of cells 18 may be used, including only one cell. The cells 18 may be positioned in any pattern between the platform 12 and the base 14. Preferably, the cells 18 are positioned in a symmetrically pattern about the geometry or configuration of the platform 12 (and base 14) so that it is easier to measure an unequal distribution on the platform.

Various types of display including one or more audible signals may be used to indicate to the user whether or not a state of equal weight distribution, or balance, is present. In the preferred embodiment shown in FIG. 2, a balance display 22 may be included in or separate from the display screen 16. However, the balance display 22 is operatively connected to the display screen 16 and, thus, a computer controller 21, so that the balance display communicates with the computer controller. In an alternative embodiment, the computer controller 21 can be operatively directly connected to the balance display 22.

The balance display 22 may include a central light or diamond 26 and an array of lights 24. Preferably, the array of lights 24 is arranged symmetrically about the central light.

When the user stands on the platform 12, the lights on the balance display 22 light up in an array indicative of the user's position with respect to the center of gravity. For example, if the user's weight is centered with respect to the four cells 18, only the central light 26 will be lit. If the user is leaning or standing too much to the right, both lights 24 to the right hand side of the central light 26 will light up. As the user leans or stands more to the left, only the single light directly to the right of the central light 26 will light up, thus indicating that the user's weight is shifted more toward the center. When the user finally shifts his weight to the center, only the central light 26 is lit. In a preferred embodiment, arrows are used as the indicators to show that weight needs to be shifted to, for example, the right and to the top of scale 10. A shifting weight in the direction of the arrows until only the center light or diamond 26 lights, thus indicates the ideal balance for actuate and repeated weight measurement. Thus, the indications of the balance display 22 is achieved by the cells sending a signal or communicating to the controller 21 that in turn sends one or more signals that result in displays of indicated movement or shifting to the balance display. Accordingly, the cells 18 are preferably in a symmetrical or balanced (equally spaced apart pattern) pattern about the configuration of platform 12 to more precisely detect each variation of weight distribution.

Different balance indicators can be used in place of the precise embodiment described above. For instance, a different array of lights can be used, and the lighting or un-lighting sequences can be reversed depending on preference. Another way of indicating balance is to provide an audible signal that signals when the user's weight is centered, when it is not, and/or to which direction the user should re-position to achieve balance.

Operation of the above-described preferred embodiment will now be described. Initially, when the scale 10 is at rest, the scale is not powered. When the user desires to use the scale 10, the user merely taps the platform 12. Tapping the platform 12 loads the cells 18 and sends a communication to the controller 21 to initiate power-on switch 28 of the type generally known, which activates a power source 30, such as a battery-powered pack. Alternatively, a manually activated power-on switch (not shown) may be provided for hand manipulation or toe-touch manipulation. After the scale 10 is powered on, the scale performs a self-zeroing routine as may be known in various existing scales. The self-zeroing routine generally signals to the controller 21 that in the instant condition, the weight output on the display screen 16 is zero. The self-zeroing operation is disclosed in a U.S. application that has been filed on Dec. 2, 2003 by the applicant of the present invention. This application is incorporated herein by reference.

Once the scale 10 has self-zeroed, the scale is now ready for the user to stand on the scale. The user then steps onto the scale 10. The balance display 22 responds to the position of the user's center of gravity by lighting up accordingly, as described above, prompting the user to re-position or shift until the central light 26 illuminates. Optionally, the controller 21 may be programmed to not display the user's weight, thus displaying a blank screen or remaining at "0", until the controller has indicated that the user's weight is centered. In lieu of, or in combination with, the visual signal, an audible signal may be produced by an audible output generator 32 that indicates relative position of the center of gravity and/or a balanced condition.

When the user's weight is sufficiently centered with respect to the load detection cells 18, the balance display 22 will indicate the balanced condition. A signal indicating that balance is achieved will prompt the controller 21 to activate the display screen 16 to display the user's weight in pounds or kilograms. When the user steps off of the scale 10, the controller 21 activates a time-out sequence to power-off the scale after a predetermined period. When the scale 10 is tapped again, the operational procedure repeats.

The scale 10 may be provided with additional features such as a display clock and calendar, a radio and/or audible signaling device, and programmable sounds.

While the preferred embodiment has been herein described, it is understood that various modifications can be made without departing from the scope of the present invention.

What is claimed is:

1. A scale for measuring the weight of an object, said scale comprising:
   an upper surface;
   a plurality of electronic sensors, each for sensing a load that is a portion of a total load applied to said upper surface of said scale by the object,
   wherein the sum of the loads of said plurality of sensors equals the total load applied to said upper surface of said scale by the object; and
   a plurality of feet, wherein each foot is positioned in a corner of said scale, wherein each of said plurality of sensors is located directly above a different one of said plurality of feet, and wherein each of said plurality of feet is movable relative to said upper surface, wherein said relative movement is in response to the load measured by said plurality of sensors.

2. The scale according to claim 1, wherein said plurality of sensors are a plurality of strain gauges.

* * * * *